United States Patent
Nishimoto et al.

(10) Patent No.: US 10,448,923 B2
(45) Date of Patent: Oct. 22, 2019

(54) AMPLIFIER CIRCUIT AND ULTRASONIC PROBE

(71) Applicant: HITACHI, LTD., Chiyoda-ku, Tokyo (JP)

(72) Inventors: Takuma Nishimoto, Tokyo (JP); Yutaka Igarashi, Tokyo (JP); Yusaku Katsube, Tokyo (JP); Kengo Imagawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 400 days.

(21) Appl. No.: 15/315,696

(22) PCT Filed: Jun. 6, 2014

(86) PCT No.: PCT/JP2014/065033
§ 371 (c)(1),
(2) Date: Dec. 1, 2016

(87) PCT Pub. No.: WO2015/186234
PCT Pub. Date: Dec. 10, 2015

(65) Prior Publication Data
US 2017/0150945 A1 Jun. 1, 2017

(51) Int. Cl.
*H03K 3/00* (2006.01)
*A61B 8/00* (2006.01)
(Continued)

(52) U.S. Cl.
CPC .......... *A61B 8/4461* (2013.01); *A61B 8/00* (2013.01); *A61B 8/461* (2013.01); *A61B 8/467* (2013.01);
(Continued)

(58) Field of Classification Search
None
See application file for complete search history.

(56) References Cited

U.S. PATENT DOCUMENTS

| 6,298,726 B1 | 10/2001 | Adachi et al. |
| 7,230,467 B1 * | 6/2007 | Gan .......... H03K 5/13 327/261 |

(Continued)

FOREIGN PATENT DOCUMENTS

| JP | 1-77034 A | 5/1989 |
| JP | 2-14612 A | 1/1990 |
| JP | 2000-5180 A | 1/2000 |

OTHER PUBLICATIONS

Partial supplementary European search report dated Jan. 2, 2018 for related European Application No. 14893777.4.
(Continued)

*Primary Examiner* — Long Nguyen
(74) *Attorney, Agent, or Firm* — Miles & Stockbridge, P.C.

(57) ABSTRACT

Amplification of a signal by a small circuit size and reduction of a power are achieved.
A current controlling current source unit 53 changes an outputting current based on a transition time setting signal tp. A current controlling current source unit 54 changes a drawing current based on a transition time setting signal tn. An amplitude control unit 55 changes a power source voltage supplied to the current controlling current source unit 53 and changes amplitude of a voltage generated by a current outputted from the current controlling current source unit 53, based on amplitude setting signal ap. An amplitude control unit 56 changes a power source voltage supplied to the current controlling current source unit 54 and changes amplitude of a voltage generated by the current drawn by the current controlling current source unit 54, based on amplitude setting signal an. The buffer unit 57 drives a load in accordance with the current outputted from the current controlling current source unit 53 and the current drawn from the current controlling current source unit 54.

7 Claims, 11 Drawing Sheets

(51) Int. Cl.
   *H03K 4/94*       (2006.01)
   *H03K 5/003*      (2006.01)
   *H03K 5/159*      (2006.01)
   *H03K 19/0175*    (2006.01)
   *H03K 3/012*      (2006.01)

(52) U.S. Cl.
   CPC .............. *A61B 8/54* (2013.01); *A61B 8/56* (2013.01); *H03K 3/012* (2013.01); *H03K 4/94* (2013.01); *H03K 5/003* (2013.01); *H03K 5/159* (2013.01); *H03K 19/017509* (2013.01)

(56) References Cited

U.S. PATENT DOCUMENTS

| 8,198,922 | B1  | 6/2012 | Chu |
|---|---|---|---|
| 2011/0199157 | A1  | 8/2011 | Kawagoshi |
| 2013/0027092 | A1* | 1/2013 | Bien ............... H03K 19/00 327/109 |

OTHER PUBLICATIONS

Humayun et al., "A Variable Range Bi-Phasic Current Stimulus Driver Circuitry for an Implantable Retinal Prosethetic Device", IEEE Journal of Solid-State Circuits, vol. 40, No. 3, Mar. 2005 pp. 763-771.

* cited by examiner

AMPLIFIER CIRCUIT AND ULTRASONIC PROBE

TECHNICAL FIELD

The present invention relates to an amplifier circuit and an ultrasonic probe.

BACKGROUND ART

Patent Literature 1 discloses an electric waveform generating circuit which is an electric waveform generating circuit including a floating source driver control circuit, a pair of switching control circuits coupled to the floating source driver control circuit, plural complementary type P type and N type MOSFETs coupled to the switching control circuit, and a converter coupled to the complementary type P type and N type MOSFETs, in which the floating source driver control circuit includes a frequency prescale unit, a control logic coupled to the frequency prescale unit, a waveform memory coupled to the frequency prescale unit, an address generator coupled to the waveform memory and the frequency prescale unit, and a pair of digital-to-analog converters coupled to the waveform memory, and one of the digital-to-analog converters is coupled to a switching current control circuit.

CITATION LIST

Patent Literature

Patent Literature 1: U.S. Pat. No. 8198922

SUMMARY OF INVENTION

Technical Problem

Incidentally, a resolution of an ultrasonic probe of ultrasonic diagnostic equipment depends on various elements, as one of the elements, the resolution depends on a size of an amplifier circuit for driving an oscillator generating an ultrasonic wave. In order to achieve a high resolution, it is requested that the size of the amplifier circuit is converged within a prescribed size. According to the circuit of Patent Literature 1, the circuit size is large, and a desired resolution of the ultrasonic probe is not achieved. Further, it is necessary to realize not only to downsize circuit but to reduce power consumption.

Hence, the present invention provides a technology which can achieve to amplify a signal by a small circuit size and to reduce power consumption.

Solution to Problem

The present application includes plural means for resolving at least a portion of the problem described above, and an example thereof is pointed out as follows. In order to resolve the problem described above, an amplifier circuit according to the present invention includes an amplifier circuit including a first current source unit for changing an outputting current based on a first setting signal, a second current source unit for changing a drawing current based on a second setting signal, a first amplitude control unit for changing a power source voltage supplied to the first current source unit and changing amplitude of a voltage generated by the current outputted from the first current source unit based on a third setting signal, a second amplitude control unit for changing a power source voltage supplied to the second current source unit and changing amplitude of a voltage generated by the current drawn by the second current source unit based on a fourth setting signal, and a buffer unit for driving a load in accordance with the current outputted from the first current source unit and the current drawn from the second current source unit.

Advantageous Effects of Invention

According to the present invention, a signal can be amplified by a small circuit size.

A problem, a configuration, and an effect other than described above will become apparent by an explanation of embodiments as follows.

DESCRIPTION OF EMBODIMENTS

Ultrasonic diagnostic equipment is widely used as an apparatus capable of observing inside of an organism easily and in real time along with X-ray CT (Computed Tomography) equipment, MRI (Magnetic Resonance Imaging) apparatus or the like. Further, in recent years, its application is enlarged by utilizing the apparatus from a conventional imaging diagnosis to a therapeutic assistance of a centesis observation, a contrast medium observation or the like, and in the ultrasonic diagnostic equipment, high image quality formation higher than conventional is requested owing to such a background. In the following, an explanation will be given of an example of applying an amplifier circuit of the present invention to a wave transmitting circuit of an ultrasonic probe of the ultrasonic diagnostic equipment.

[First Embodiment]

Figure 1:
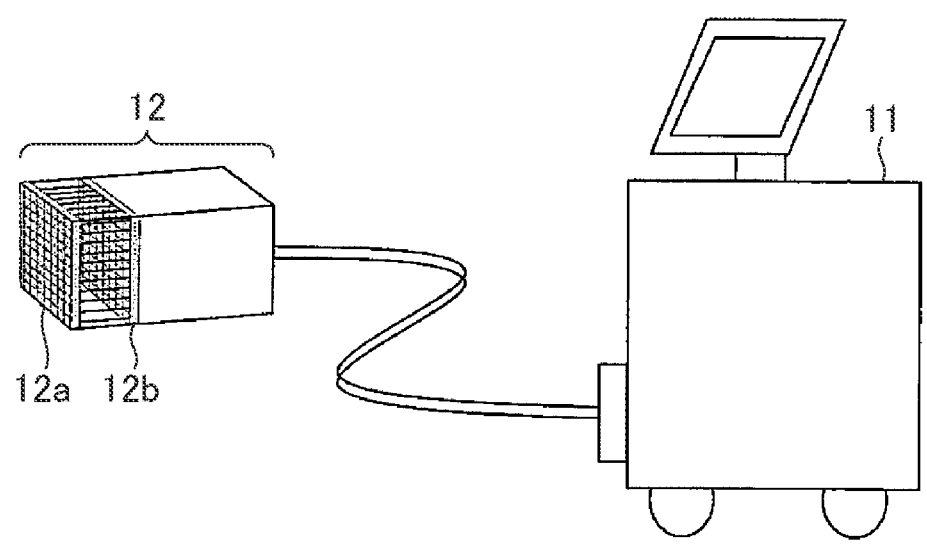
FIG. 1 is a view showing ultrasonic wave diagnostic equipment according to a first embodiment.

FIG. 1 is a view showing ultrasonic diagnostic equipment according to a first embodiment of the present invention. As shown in FIG. 1, the ultrasonic diagnostic equipment includes an apparatus main body 11 and an ultrasonic probe 12.

The apparatus main body 11 includes, for example, a CPU (Central Processor Unit) for controlling a total of the ultrasonic diagnostic equipment, a memory of a HDD (Hard Disk Drive) storing a program or the like executed by the CPU, an RAM for temporarily storing data to be processed, and a communication IF (IF: InterFace) apparatus for communicating with an exterior apparatus at an inner portion of its cabinet. Further, the apparatus main body 11 includes, for example, various kinds of power source circuits, and an image processing circuit for subjecting a signal from an ultrasonic probe to image processing in the inner portion of the cabinet. Further, the apparatus main body 11 includes, for example, an input apparatus of a keyboard, a mouse or the like, and an output apparatus of a liquid crystal display apparatus or the like. The input apparatus maybe a touch panel provided at the liquid crystal display apparatus. The apparatus main body 11 is constructed by a structure movable on a floor face freely by a caster or the like attached to the floor face.

The ultrasonic probe 12 includes a 2D (Dimension) array oscillator 12a, and a 2D array IC (Integrated Circuit) 12b. The 2D array oscillator 12a includes plural oscillators emitting an ultrasonic wave at a face of the ultrasonic wave probe 12 on a side of being brought into contact with the human body. The plural oscillators of the 2D array oscillators 12a are arranged two-dimensionally (planar shape).

The 2D array IC 12b includes plural circuits of driving the oscillators of the 2D array oscillator 12a to be opposed to the 2D array oscillator 12a. The plural circuits of the 2D array IC 12b are two-dimensionally arranged.

The plural circuits of the 2D array IC 12b are provided in correspondence with the plural oscillators of the 2D array oscillator 12a. For example, one circuit of the 2D array IC 12b is electrically connected to one oscillator of the 2D array oscillator 12a.

Figure 2:
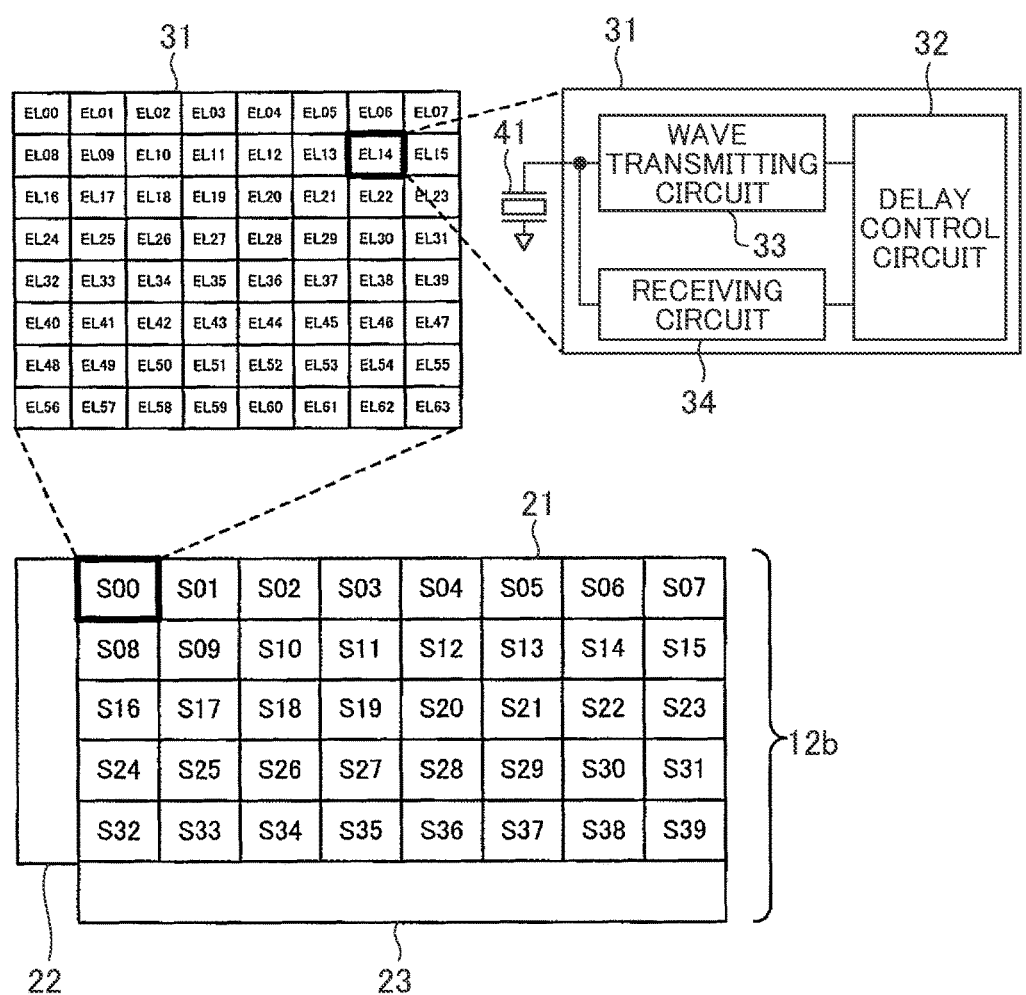
FIG. 2 is a diagram for explaining a 2D array IC of FIG. 1.

FIG. 2 is a diagram for explaining the 2D array IC of FIG. 1. FIG. 2 shows the 2D array IC 12b shown in FIG. 1. As shown in a lower portion of FIG. 2, the 2D array IC 12b includes plural sub arrays 21, and surrounding circuits 22, and 23.

The sub array 21 and the surrounding circuits 22 and 23 are formed, for example, on one IC substrate. In FIG. 2, 40 (S00 through S39) of the sub arrays 21 are formed on the IC substrate. Further, in FIG. 2, two of the surrounding circuits 22 and 23 are formed on the IC substrate.

The surrounding circuits 22 and 23 include IF circuits for communicating the apparatus main body 11, although not illustrated. Further, the surrounding circuits 22 and 23 include a common low voltage power source circuit and a common high voltage power source circuit for supplying power sources to the plural sub arrays 21, although not illustrated. Further, the surrounding circuits 22 and 23 include a control circuit for controlling the plural sub arrays 21 based on a designation from the apparatus main body 11, although not illustrated.

As shown on a left side of an upper portion of FIG. 2, each of the plural sub arrays 21 includes plural element circuits 31. In FIG. 2, an example of the element circuits 31 of the sub array 21 of "S00" is shown. One of the sub array 21 includes 64 (EL00 through EL63) of the element circuit 31.

The plural oscillators of the 2D array oscillator 12a are downsized in accordance with a request for high image quality formation, and the number thereof is increased. In accordance therewith, the number of the element circuits 31 reaches, for example, about ten thousand. Therefore, it is important to reduce a size and power consumption of the element circuit 31. Further, in FIG. 2, an example of 40 (S00 through S39)×64 (EL00 through EL63) of the element circuits 31 is shown by simplifying illustration.

As shown on a right side of an upper portion of FIG. 2, each of the plural element circuits 31 includes a delay control circuit 32, a wave transmitting circuit 33, and a receiving circuit 34. In FIG. 2, a circuit block example of the element circuit 31 of "EL14" is shown. Further, FIG. 2 also shows an oscillator 41 of the 2D array oscillator 12a connected to the element circuit 31.

The element circuits 31 (for example, EL00 through EL07 etc.) of the same row are connected to a common low voltage power source circuit and a common high voltage power source circuit, not illustrated, described above, included by the surrounding circuits 22 and 23. For example, the element circuits 31 of the same row are connected to a pair of positive and negative low voltage power source wirings. Further, the element circuits 31 of the same row are connected to a pair of positive and negative high voltage power source wirings. In the following, the low voltage positive side power source wiring may be referred to as power source VDD and the negative side low voltage power source wiring may be referred to as power source VSS. Further, the high voltage positive side power source wiring may be referred to as power source HVDD, and the high voltage negative side power source wiring may be referred to as power source HVSS.

The delay control circuit 32 controls an output timing of a drive signal for driving the oscillator 41 outputted from the wave transmitting circuit 33 in accordance with a control from the apparatus main body 11. For example, the delay control circuit 32 controls the output timing of the drive signal outputted by the wave transmitting circuit 33 to scan a focus point of plural ultrasonic waves (point at which ultrasonic waves are overlapped) outputted by the plural oscillators of the 2D array oscillator 12a. Further, the delay control circuit controls a receiving timing of the receiving circuit 34 such that a pertinent image of a target is obtained from plural reflected waves received by, for example, the plural oscillators of the 2D array oscillator 12a. The delay control circuit 32 transmits a signal of a reflected wave received by the receiving circuit 34 to the apparatus main body 11. Thereby, the apparatus main body 11 can display an image of the target to the output apparatus by subjecting the signal received from the delay control circuit 32 to image processing.

The wave transmitting circuit 33 outputs the drive signal for driving the oscillator 41 based on the signal outputted from the delay control circuit 32. The wave transmitting circuit 33 can make amplitude of the drive signal outputted to the oscillator 41 variable. Further, the wave transmitting circuit 33 is made to be able to adjust a transition time of a rise and a transition time of a fall of the drive signal outputted to the oscillator 41.

The receiving circuit 34 amplifies the signal received by the oscillator 41 to output to the delay control circuit 32.

Figure 3:
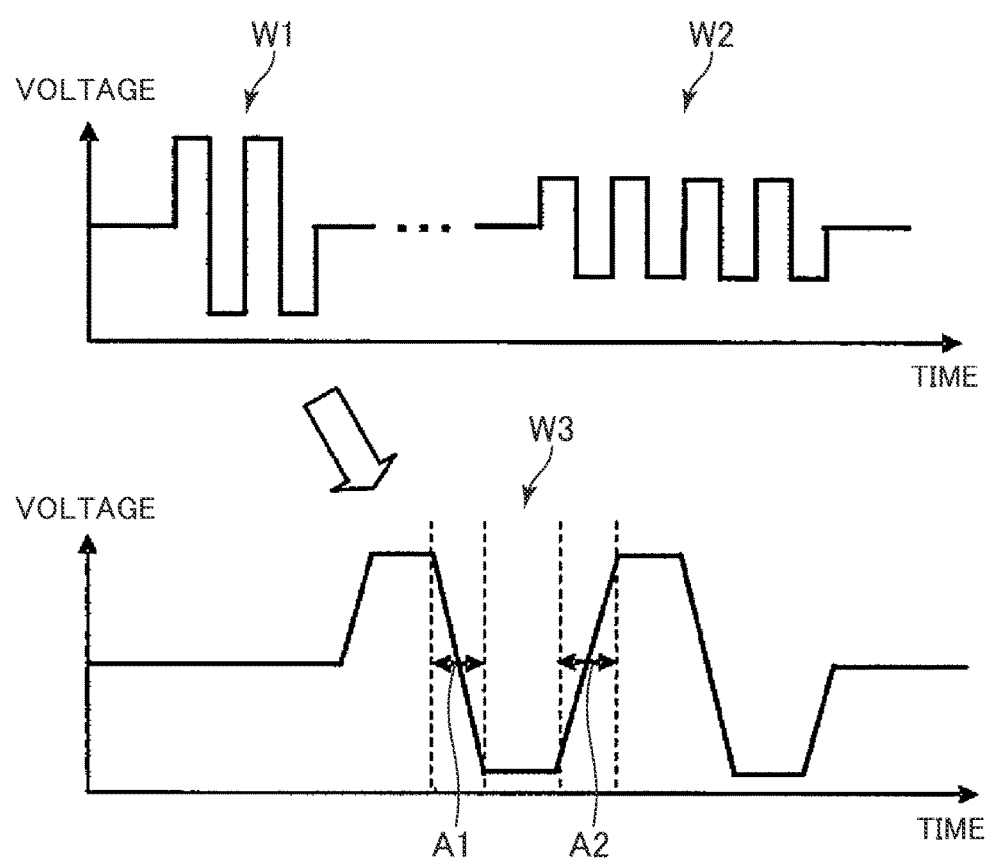
FIG. 3 is a diagram for explaining amplitude variable and transition time adjustment of a wave transmitting circuit of FIG. 2.

FIG. 3 is a diagram for explaining amplitude variable and transition time adjustment of the wave transmitting circuits of FIG. 2. FIG. 3 shows waveforms W1 and W2 of drive signals which are outputted by the wave transmitting circuit 33 to the oscillator 41. Further, FIG. 3 shows a waveform W3 enlarging the waveform W1.

The wave transmitting circuit 33 is made to be able to make amplitude of a drive signal variable in accordance with a diagnosed portion or a kind of a described image. For example, in a case where the apparatus main body 11 displays a lamina image on a display apparatus, the wave transmitting circuit 33 outputs a drive signal of amplitude indicated by the waveform Who the oscillator 41. Further, for example, in a case where the apparatus main body 11 displays a blood flow image on the display apparatus, the wave transmitting circuit 33 outputs a drive signal of the waveform W2 of amplitude smaller than amplitude of the waveform W1 to the oscillator 41.

When the transition time of the rise of the drive signal and the transition time of the fall thereof differ from each other, a virtual image (artifact) is generated at the lamina image or the blood flow image. Therefore, the wave transmitting circuit 33 is made to be able to adjust the transition time of the rise and the transition time of the fall of the drive signal equal to each other. For example, the wave transmitting circuit 33 is made to be able to adjust the transition time of the fall of the drive signal indicated by an arrow mark A1 of FIG. 3 and the transition time of the rise of the drive signal indicated by an arrow mark A2. The wave transmitting circuit 33 is made to be able to adjust a transition time similarly with regard to a waveform W2.

Here, although a resolution of an ultrasonic probe depends on various elements, as one thereof, the resolution depends on a size of the oscillator 41. For example, smaller the size of the oscillator 41, the more densely the target can be scanned, and a spatial resolution of the lamina image or the blood flow image is improved. Therefore, a size of, for example, 200 through 300 $\mu m^2$ per piece is requested for the oscillator 41.

As described above, the element circuit 31 is connected to the oscillators 41 in a one-to-one relationship. Therefore, a size similar to a size of the oscillator 41 is requested for the size of the element circuit 31. For example, a size of 200 through 300 $\mu m^2$ per piece is requested for the element circuit 31.

The wave transmitting circuit 33 is made to be able to make the amplitude of the drive signal variable. Further, the wave transmitting circuit 33 is made to be able to adjust the transition time of the drive signal. Therefore, although the single element circuit 31 includes the delay control circuit 32, the wave transmitting circuit 33, and the receiving circuit 34, the wave transmitting circuit 33 occupies about a half of the size. Therefore, it is requested to reduce the size of the wave transmitting circuit 33 and reduce the power consumption in order to obtain the ultrasonic probe having the high resolution.

Figure 4:
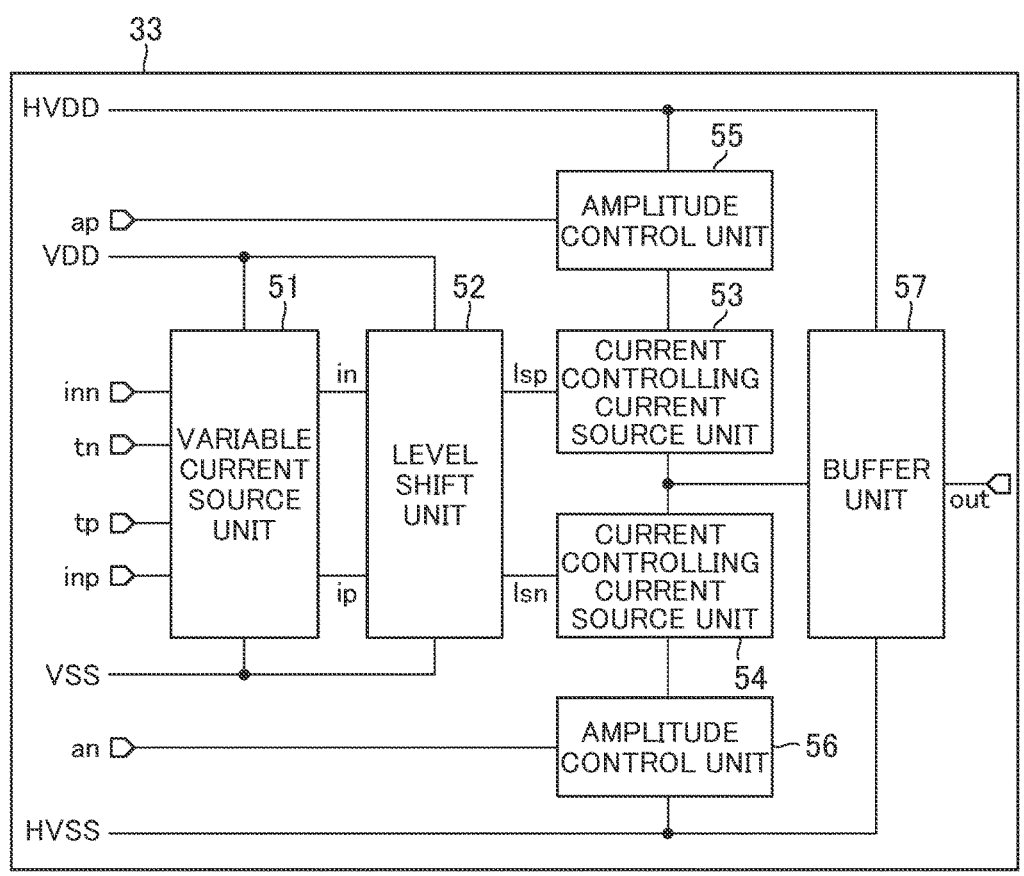
FIG. 4 is a diagram showing a block example of the wave transmitting circuit of FIG. 2.

FIG. 4 is a diagram showing a block example of the wave transmitting circuit of FIG. 2. As shown in FIG. 4, the wave transmitting circuit 33 includes a variable current source unit 51, a level shift unit 52, current controlling current source units 53 and 54, amplitude control units 55 and 56, and a buffer unit 57.

The variable current source unit 51 is connected to power sources VDD and VSS. An input signal inp is inputted to the variable current source unit 51. The input signal inp is outputted from the delay control circuit 32 explained in reference to FIG. 2. For example, the input signal inp is a positive pulse signal. When the input signal inp is inputted to the variable current source unit 51, for example, a drive signal out of a positive pulse a power of which is amplified is outputted from the buffer unit 57.

An input signal inn is inputted to the variable current source unit 51. The input signal inn is outputted from the delay control circuit 32 explained in reference to FIG. 2. For example, the input signal inn is a positive pulse signal. When the input signal inn is inputted to the variable current source unit 51, for example, a drive signal out of a negative pulse a power of which is amplified is outputted from the buffer unit 57.

A transition time setting signal tp is inputted to the variable current source unit 51. The transition time setting signal tp is a signal for adjusting a transition time of a rise of the drive signal out outputted from the buffer unit 57. The transition time of the rise of the drive signal is adjusted, for example, in accordance with a magnitude of a voltage of the transition time setting signal tp.

The transition time setting signal tp is outputted from, for example, the apparatus main body 11. A magnitude of the transition time setting signal tp is made variable, for example, by operating the input apparatus of the apparatus main body 11 by a user. That is, the user can adjust the transition time of the rise of the drive signal out outputted from the buffer unit 57. The variable current source unit 51 outputs a signal ip of a current in accordance with a magnitude of the transition time setting signal tp to the level shift unit 52, for example, while an input signal inp of a positive pulse is being inputted.

A transition time setting signal tn is inputted to the variable current source unit 51. The transition time setting signal tn is a signal for adjusting the transition time of the fall of the drive signal out outputted from the buffer unit 57. The transition time of the fall of the drive signal out is adjusted, for example, in accordance with a magnitude of a voltage of the transition time setting signal tn.

The transition time setting signal tn is outputted from, for example, the apparatus main body 11. A magnitude of the transition time setting signal tn is made variable by, for example, operating the input apparatus of the apparatus main body 11 by the user. That is, the user can adjust the transition time of the rise of the drive signal out outputted from the buffer unit 57. The variable current source unit 51 outputs a signal in of a current in accordance with a magnitude of the transition time setting signal to to the level shift unit 52, for example, while the input signal inn of the positive pulse is being inputted.

The level shift unit 52 is connected to power sources VDD and VSS. The level shift unit 52 shifts a level of a signal ip outputted from the variable current source unit 51 to a level of a high voltage, and outputs a signal Isp to the current controlling current source unit 53. Further, the level shift unit 52 shifts a level of a signal in outputted from the variable current source unit 51 to a level of a high voltage signal, and outputs a signal Isn to the current controlling current source unit 54.

The signal Isp outputted from the level shift unit 52 is inputted to the current controlling current source unit 53. The current controlling current source unit 53 changes a current outputted to the buffer unit 57 based on a magnitude of the signal Isp. For example, the larger the current of the signal Isp outputted from the level shift unit 52, the larger the current outputted to the buffer unit 57 by the current controlling current source unit 53. The larger the current outputted from the current controlling current source unit 53 to the buffer unit 57, the shorter the transition time of the rise of the drive signal out outputted from the buffer unit 57.

Further, the signal Isp is made by shifting a level of the signal ip, its magnitude is based on a magnitude of the transition time setting signal tp. Therefore, the current controlling current source unit 53 changes a current outputted to the buffer unit 57 based on the magnitude of the transition time setting signal tp set by the user.

A signal Isn outputted from the level shift unit 52 is inputted to the current controlling current source unit 54.

The current controlling current source unit 54 changes a current drawn from the buffer unit 57 based on the magnitude of the signal Isn. For example, the larger the current of the signal Isn outputted from the level shift unit 52, the larger the current drawn by the current controlling current source unit 53 from the buffer unit 57. The larger the current drawn from the buffer unit 57 of the current controlling current source unit 54, the shorter the transition time of the fall of the drive signal out outputted from the buffer unit 57.

Further, the signal Isn is made by shifting a level of the signal in, and its magnitude is based on the magnitude of the transition time setting signal tn. Therefore, the current controlling current source unit 53 changes the current drawn from the buffer unit 57 based on the magnitude of the transition time setting signal tn set by the user.

The amplitude control unit 55 is connected between the power source HVDD and the current controlling current source unit 53. An amplitude setting signal ap is inputted to the amplitude control unit 55. The amplitude setting signal ap is a signal for making amplitude of a rise of the drive signal out outputted from the buffer unit 57 variable. The amplitude of the rise of the drive signal out is made variable in accordance with a magnitude of the amplitude setting signal ap.

The amplitude setting signal ap is outputted from, for example, the apparatus main body 11. The magnitude of the amplitude setting signal ap is made variable, for example, by operating an input apparatus of the apparatus main body 11 by the user. That is, the user can make the amplitude of the rise of the drive signal out outputted from the buffer unit 57 variable.

The amplitude control unit 55 changes a power source voltage supplied to the current controlling current source unit 53 based on a magnitude of the amplitude setting signal ap, and changes amplitude of a voltage generated by a current outputted from the current controlling current source unit 53. For example, when an absolute value of the power source voltage supplied to the current controlling current source unit 53 is reduced, amplitude of a voltage generated by a current outputted from the current controlling current source unit 53 (input voltage of buffer unit 57) is recued. Further, amplitude of a rise of the drive signal out outputted from the buffer unit 57 is reduced.

The amplitude control unit 56 is connected between the power source HVSS and the current controlling current control unit 54. An amplitude setting signal an is inputted to the amplitude control unit 56. The amplitude setting signal an is a signal for making amplitude of a fall of the drive signal out outputted from the buffer unit 57 variable. The amplitude of the fall of the drive signal out is made variable in accordance with a magnitude of the amplitude setting signal an.

The amplitude setting signal an is outputted from, for example, the apparatus main body 11. A magnitude of the amplitude setting signal an is made variable by, for example, operating the input apparatus of the apparatus main body 11 by the user. That is, the user can make the amplitude of the fall of the drive signal out outputted from the buffer unit 57 variable.

The amplitude control unit 56 changes a power source voltage supplied to the current controlling current source unit 53 based on a magnitude of the amplitude setting signal an, and changes amplitude of a voltage generated by a current drawn by the current controlling current source unit 54. For example, when an absolute value of a power source voltage supplied to the current controlling current source unit 54 is reduced, amplitude of a voltage generated by a current drawn by the current controlling current source unit (input voltage of buffer unit 57) is reduced. Further, the amplitude of the fall of the drive signal out outputted from the buffer unit 57 is reduced.

The buffer unit 57 is connected to the power sources HVDD and VHSS. In the buffer unit 57, an input unit for inputting a signal is connected to a connecting point of current controlling current source units 53 and 54 which are connected in series. The buffer unit 57 outputs the drive signal out to the oscillator 41 in accordance with a current outputted from the current controlling current source unit 53 and a current drawn by the current controlling current source unit 54.

Figure 5:
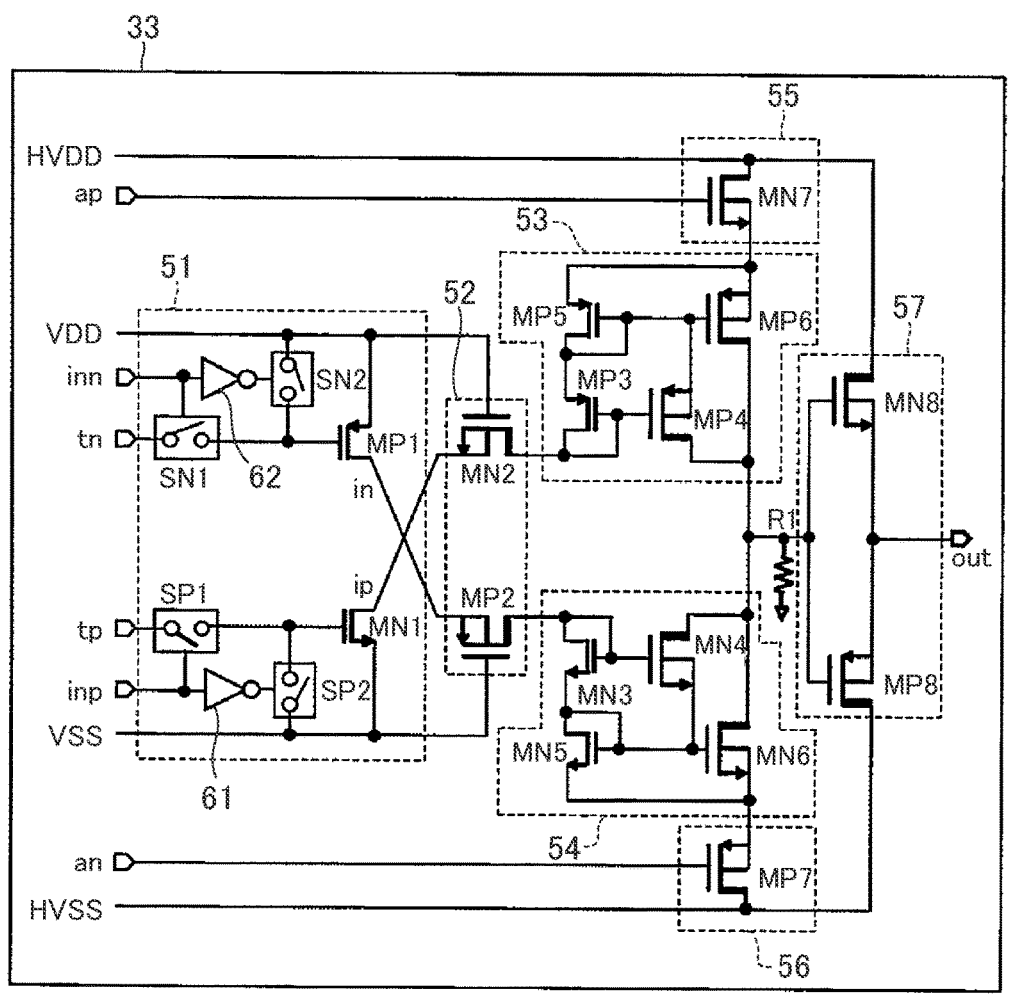
FIG. 5 is a diagram showing a circuit example of the wave transmitting circuit of FIG. 4.

FIG. 5 is a diagram showing a circuit example of the wave transmitting circuit of FIG. 4. FIG. 5 shows circuit examples of the variable current source unit 51, the level shift unit 52, the current controlling current source units 53 and 54, the amplitude control units 55 and 56, and the buffer unit 57 shown in FIG. 4.

The variable current source unit 51 includes switches SP1, SP2, SN1, and SN2, inverters 61, 62, a transistor MN1 of NMOS (Negative channel metal Oxide Semiconductor) and a transistor MP1 of PMOS (Positive channel metal Oxide Semiconductor).

The switch SP1 is inputted with an input signal inp and a transition time setting signal tp. The switch SP1 opens or closes the switch in accordance with the input signal inp, and outputs or does not output the inputted transition time setting signal tp to a gate of the transistor MN1. For example, the switch SP1 closes the switch when the input signal inp is inputted from the delay control circuit 32 (when the input signal of "H state" is outputted), and outputs the transition time setting signal tp to the gate of the transistor MN1.

The inverter 61 is inputted with the input signal inp. The inverter 61 reverses the input signal inp to output to the switch SP2. For example, the inverter 61 outputs a signal of "L state" to the switch SP2 when the input signal inp of "H state" is inputted.

The switch SP2 is inputted with the input signal inp reversed by the inverter 61 and a voltage of the power source VSS. The switch SP2 opens or closes the switch in accordance with the input signal inp reversed by the inverter 61 and outputs or does not output an inputted voltage of a power source VSS to the gate of the transistor MN1. For example, the switch SP2 closes the switch and outputs the voltage of the power source VSS to the gate of the transistor MN1 in a case where the input signal inp is not outputted from the delay control circuit 32 to the inverter 61 (in a case where the input signal inp of "L state" is outputted to the inverter 61).

The gate of the transistor MN1 is connected to the switches SP1 and SP2. A source of the transistor MN1 is connected to the power source VSS. A drain of the transistor MN1 is connected to a transistor MN2 of the level shift unit 52.

When the input signal inp is outputted from the delay control circuit 32, the gate of the transistor MN1 is inputted with the transition time setting tp. For example, when the input signal inp of "H state" is outputted from the delay control circuit 32, the switch SP1 is closed, the switch SP2 is opened, and the gate of the transistor MN1 is inputted with the transition time setting signal tp. When the transition time setting signal tp is inputted to the gate of the transistor MN1, the transistor MN1 is made ON, and makes a current in accordance with a voltage of the transition time setting signal tp flow between the drain and the source. On the other hand, in a case where the input signal inp is not outputted from the delay control circuit 32, the gate of the transistor MN1 is inputted with a voltage of the power source VSS. For example, in a case where the input signal inp of "L state" is outputted from the delay control circuit 32, the switch SP1 is opened, the switch SP2 is closed, and the gate of the transistor MN1 is inputted with the voltage of the power source VSS. When the voltage of the power source VSS is inputted to the gate of the transistor MN1, the transistor MN1 is made OFF, and does not make a current flow between the drain and the source.

The switch SN1 is inputted with an input signal inn and a transition time setting signal tn. The switch SN1 opens or closes the switch in accordance with the input signal inn, and outputs or does not output the inputted transition time setting signal tn to a gate of the transistor MP1. For example, the switch SN1 closes the switch when the input signal inn is outputted from the delay control circuit 32 (when the input signal inn of "H state" is outputted), and outputs the transition time setting signal to a gate of the transistor MP1.

The inverter 62 is inputted with the input signal inn. The inverter 62 reverses the inputted input signal inn to output to the switch SN1. For example, when the inverter 62 is inputted with the input signal inn of "H state", the inverter 62 outputs a signal of "L state" to the switch SN2.

The switch SN2 is inputted with the input signal inn reversed by the inverter 62 and a voltage of a power source VDD. The switch SN2 opens or closes the switch in accordance with the input signal inn reversed by the inverter 62, and outputs or does not output the inputted voltage of the power source VDD to a gate of the transistor MP1. For example, in a case where the input signal inn do not output from the delay control circuit 32 to the inverter 62 (in a case where the input signal inn of "L state" is outputted to the inverter 62), the switch SN2 closes the switch, and outputs the voltage of the power source VDD to the gate of the transistor MN1.

The gate of the transistor MP1 is connected to the switches SN1 and SN2. A source of transistor MP1 is connected to the power source VDD. A drain of the transistor MP1 is connected to the transistor MP2 of the level shift unit 52.

When the input signal inn is outputted from the delay control circuit 32, the gate of the transistor MP1 is inputted with the transition time setting signal tn. For example, when the input signal inn of "H state" is outputted from the delay control circuit 32, the switch SN1 is closed, the switch SP2 is opened, and the gate of the transistor MP1 is inputted with a transition time setting signal tn. The transistor MP1 is made ON when the transition time setting signal tn is inputted to the gate, and makes a current in accordance with a voltage of the transition time setting signal tn flow between the drain and the source. On the other hand, in a case where the input signal inn is not outputted from the delay control circuit 32, the gate of the transistor MP1 is inputted with the voltage of the power source VDD. For example, in a case where the input signal inn of "L state" is outputted from the delay control circuit 32, the switch SN1 is opened, the switch SN2 is closed, and the gate of the transistor MP1 is inputted with the voltage of the power source VDD. When the gate of the transistor MP1 is inputted with the voltage of the power source VDD, the transistor MP1 is made OFF and does not make a current flow between the drain and the source.

The level shift unit 52 includes a transistor MN2 of NMOS for high voltage withstanding use and a transistor MP2 of PMOS for voltage withstanding use.

A gate of the transistor MN2 is connected to the power source VDD. A source of the transistor MN2 is connected to a drain of the transistor MN1 of the variable current source unit 51. A drain of the transistor MN2 is connected to a gate and a drain of a transistor MP3 of the current controlling current source unit 53.

The transistor MN2 is made ON when the transistor MN1 is made ON and a voltage of the source is reduced. Thereby, a current in accordance with a magnitude of the transition time setting signal tp inputted to the gate of the transistor MN1 is made to flow between the drain and the source of the transistor MN2.

A gate of the transistor MP2 is connected to the power source VSS. A source of the transistor MP2 is connected to a drain of the transistor MP1 of the variable current source unit 51. A drain of the transistor MP2 is connected to a gate a drain of a transistor MN3 of the current controlling current source unit 54.

The transistor MP2 is made ON when the transistor MP1 is made ON and a voltage of the source is increased. Thereby, a current in accordance with a magnitude of a transition time setting signal to inputted to the gate of the transistor MP1 is made to flow between the drain and the source of the transistor MP2.

The current controlling current source unit 53 includes transistors MP3 and MP5 of PMOS and transistors MP4 and MP6 of PMOS for high voltage withstanding use.

The transistor MP3 is diode-connected. A gate of the transistor MP3 is connected to a gate of the transistor MP4.

A source of the transistor MP4 is connected to gates of the transistor MP5 and MP6. A drain of the transistor MP4 is connected to a drain of the transistor MP6, drains of transistor MN4 and MN6 of the current controlling current source unit 54, and gates of transistors MN8 and MP8 of the buffer unit 57.

The transistor MP5 is diode-connected. A gate of the transistor MP5 is connected to the gate of the transistor MP6, and the source of the transistor MP4. A source of the transistor MP5 is connected to a source of the transistor MP6 and a source of a transistor MN7 of the amplitude control unit 55.

The transistors MP5 and MP6 make a current in accordance with currents flowing in MP5, MP3, MN2 and MN1 flow to the transistor MP6. At that occasion, the transistors MP5 and MP6 amplify the currents flowing in the transistors MP5, MP3, MN2, and MN1 to flow to the transistor MP6. An amplification rate can be set by, for example, aspect ratios of the transistors MP5 and MP6. The transistor MP3 and MP4 shorten a response time of a current of the transistor MP6 in contrast to currents flowing in the transistors MP5, MP3, MN2 and MN1.

Here, the larger the voltage of the transition time setting signal tp, the larger the currents flowing in the transistors MP5, MP3, MN2, and MN1. The current controlling current source unit 53 is a current controlling current source for controlling a current flowing in the transistor MP6 in accordance with currents flowing in the transistors MP5 and MP3, and when the currents flowing in the transistors MP5, MP3, MN2 and MN1 are increased, also a current outputted from the transistor MP6 to the gates of the transistors MN8 and MP8 of the buffer unit 57 are increased. Thereby, charge times of the gates of the transistors MN8 and MP8 of the buffer unit 57 are shortened, and a rise time of the voltage is accelerated.

The current controlling current source unit 54 includes transistors MN3 and MN5 of NMOS and transistors MN4 and MN6 of NMOS for high voltage withstanding use.

The transistor MN3 is diode-connected. A gate of the transistor MN3 is connected to the gate of the transistor MN4.

A source of the transistor MN4 is connected to gates of the transistors MN5 and MN6. A drain of the transistor MN4 is connected to the drain of the transistor MN6, drains of the transistors MP4 and MP6 of the current controlling current source unit 53, and gates of the transistors MN8 and MP8 of the buffer unit 57.

The transistor MN5 is diode-connected. A gate of the transistor MN5 is connected to a gate of the transistor MN6, and a source of the transistor MN4. A source of the transistor MN5 is connected to a source of the transistor MN6, and a source of the transistor MP8 of the amplitude control unit 56.

The transistors MN5 and MN6 make a current in accordance with currents flowing in the transistors MP1, MP2, MN3, and MN5 flow to the transistor MN6. At that time, the transistors MN5 and MN6 amplify currents flowing in the transistors MP1, MP2, MN3, and MN5 to flow to the transistor MN6. An amplification rate can be set by, for example, aspect ratios of the transistors MN5 and MN6. The transistors MN3 and MN4 shorten a response time of a current of the transistor MN6 for currents flowing in the transistors MP1, MP2, MN3, and MN5.

Here, the smaller the voltage of the transition time setting signal tn, the larger the currents flowing in the transistors MP1, MP2, MN3, and MN5. The current controlling current source unit 54 is a current controlling current source for controlling a current flowing in the transistor MN6 in accordance with currents flowing in the transistors MN3 and MN5, and when currents flowing in the transistors MP1, MP2, MN3, and MN5 are increased, also currents drawn from gates of the transistors MN8 and MP8 of the buffer unit 57 to the transistor MP6 are increased. Thereby, discharge times of the gates of the transistors MN8 and MP8 of the buffer unit 57 are shortened, and a fall time of the voltage is accelerated.

The amplitude control unit 55 includes a transistor MN7 of NMOS for high withstanding voltage use. A gate of the transistor MN7 is inputted with amplitude setting signal ap. A drain of the transistor MN7 is connected to the power source HVDD. A source of the transistor MN7 is connected to sources of the transistors MP5 and MP6 of the current controlling current source unit 53.

When a current flows in the transistor MP6, gate voltages of the transistors MN8 and MP8 of the buffer unit 57 rise and also a source voltage of the transistor MP6 rises. When a voltage of amplitude setting signal ap inputted to the gate of the transistor MN7 is made to be "apv", and a threshold voltage of the transistor MN7 is made to be "Vthn", a source voltage of the transistor MP6 rises to a vicinity of "apv-Vthn". "Vthn" is a fixed value, and therefore, the source voltage of the transistor MP6 can be made variable by changing "apv". That is, the transistor MN7 can make amplitude when gate voltages of the transistors MN8 and MP8 of the buffer unit 57 rise variable. Further, when the source voltage of the transistor MP6 rises to a vicinity of "apv-Vthn", a current flowing in the transistor MP6 flows in a resistor R1 one end of which is connected to the power source VSS.

The amplitude control unit 56 includes a transistor MP7 of PMOS for a high withstanding voltage use. A gate of the transistor MP7 is inputted with the amplitude setting signal an. A drain of the transistor MP7 is connected to the power source HVSS. A source of the transistor MP7 is connected to sources of the transistors MN5 and MN6 of the current controlling current source unit 57.

When a current flows in the transistor MN6, gate voltages of the transistor MN8 and MP8 of the buffer unit 57 fall, and also a source voltage of the transistor MN6 falls. When a voltage of the amplitude setting signal an inputted to the gate of the transistor MP7 is made to be "anv", and a threshold voltage of the transistor MP7 is made to be "Vthp", the source voltage of the transistor MN6 falls to a vicinity of "anv+Vthp". "Vthp" is a fixed value, and therefore, a source voltage of the transistor MN6 can be made variable by changing "anv". That is, the transistor MP7 can make amplitude when the gate voltages of the transistors MN8 and MP8 of the buffer unit 57 fall variable in accordance with a voltage "any" of the amplitude setting signal inputted to the gate. Further, when the source voltage of the transistor MN6 falls to a vicinity of "anv+Vthp", the transistor MN6 draws a current from the resistor R1 an end of which is connected to the power source VSS.

The buffer unit 57 includes the transistor MN8 of NMOS for high voltage withstanding use, and the transistor MP8 of PMOS for high voltage withstanding use.

Gates of the transistors MN8 and MP8 are connected to the drains of the transistors MP4 and MP6 of the current controlling current source unit 53. Further, gates of the transistors MN8 and MP8 are connected to the drains of the transistors MN4 and MN6 of the current controlling current source unit 54. Further, the gate of the transistors MN8 and MP8 are connected to other end of the resistor R1 one end of which is connected to the power source VSS.

The drain of the transistor MN8 is connected to the power source HVDD. The source of the transistor MN8 is connected to the source of the transistor MP8, and is connected to the oscillator 41, not illustrated. The drain of the transistor MP8 is connected to the power source HVSS.

The transistor MN8 is made ON when a current is outputted from the current controlling current source unit 53. Thereby, a current flow from the power source HVDD to the oscillator 41. The transistor MP8 is made ON when the current controlling current source unit 53 draws a current. Thereby, the current is drawn from the oscillator 41 to the power source HVSS.

Sizes of the transistors MN8 and MP8 for high withstanding voltage use are larger than those of the transistors MN2, MP2, MP4, MP6, MN7, MN4, MN6, and MP7 for high voltage withstanding use, and large currents can be made to flow to the transistors MN8 and MP8. For example, the transistors MN8 and MP8 include sizes ten times as much as the sizes of transistors MN2, MP2, MP4, MP6, MN7, MN4, MN6, and MP7. The transistors MN2, MP2, MP4, MP6, MN7, MN4, MN6, and MP7 make currents of, for example, several mA flow, whereas the transistors MN8 and MP8 can make several tens mA flow.

Further, sizes of the transistors MN1, MP1, MP3, MN3, and MN5 which are not for high voltage withstanding use are smaller than sizes of the transistor for high voltage withstanding use. Also, sizes of the transistors configuring the switches SP1, SP2, SN1, and SN2 as well as the transistors configuring the inverters 61 and 62 are smaller than the sizes of the transistors for high voltage withstanding use.

An operation of the wave transmitting circuit 33 of FIG. 5 will be explained in reference to timing charts.

Figure 6:
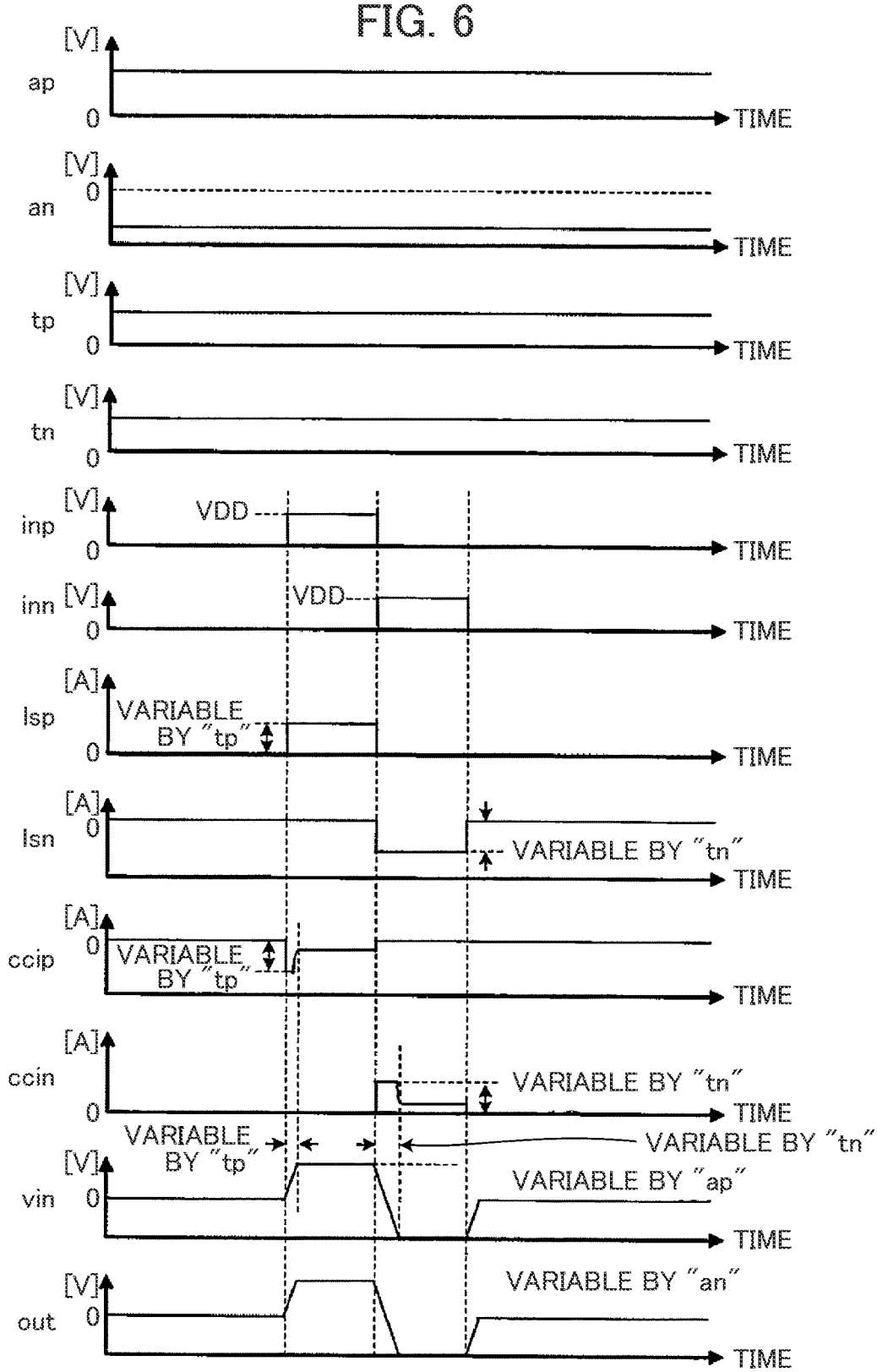
FIG. 6 is a diagram part 1 showing a timing chart of the wave transmitting circuit of FIG. 5.

FIG. 6 is part 1 of a diagram showing timing charts of wave transmitting circuit of FIG. 5. "ap" shown in FIG. 6 shows a voltage of amplitude setting signal ap inputted to the gate of the transistor MN7 of the amplitude control unit 55.

"an" shows a voltage of amplitude setting signal an inputted to the gate of the transistor MN7 of the amplitude control unit 56.

"tp" shows a voltage of the transition time setting signal tp inputted to the switch SP1 of the variable current source unit 51.

"tn" shows a voltage of the transition time setting signal tn inputted to the switch SN1 of the variable current source unit 51.

"inp" shows a voltage of the input signal inp inputted to the switch SP1 and the inverter 61 of the variable current source unit 51.

"inn" shows a voltage of the input signal inn inputted to the switch SN1 and the inverter 62 of the variable current source unit 51.

"Isp" shows a current flowing in the transistor MN2 of the level shift unit 52. As shown in FIG. 6, the current "Isp" flows in the transistor MN2 of the level shift unit 52 when the input signal inp of the voltage VDD (H state) is inputted. A magnitude of the current "Isp" is made variable by a magnitude of a voltage of the transition time setting signal tp inputted to the gate of the transistor MN1 via the switch SP1.

"Isn" shows a current flowing in the transistor MP2 of the level shift unit 52. As shown in FIG. 6, the current "Isn" flows in the transistor MP2 of the level shift unit 52 when the input signal inn of the voltage VDD (H state) is inputted. A magnitude of the current "Isn" is made variable by a magnitude of a voltage of the transition time setting signal to inputted to the gate of the transistor MP1 via the switch SN1.

"ccip" shows a current outputted from the current controlling current source unit 53 to the buffer unit 57. A current indicated in "ccip" is outputted from the current controlling current source unit 53 to the buffer unit 57 by making a current "Isp" flow to the transistor MN2 of the level shift unit 52. An amplitude (magnitude of current) of the current "ccip" is made variable by a magnitude of the voltage of the transition setting signal tp.

The current "ccip" flows first the gates of the transistors MN8 and MP8 of the buffer unit 57, and therefore, as shown in FIG. 6, a current having a large absolute value flows at first. Thereafter, the absolute value of the current "ccip" is gradually reduced while electric charges are charged to the gates of the current transistors MN8 and MP8. Further, the current "ccip" flows in the resistor R1 by a constant current value.

"ccin" shows a current drawn by the current controlling current source unit 54 from the buffer unit 57. The current controlling current unit 54 draws a current indicated by "ccin" from the buffer unit 57 by making the current "ccin" flow to the transistor MP2 of the level shift unit 52. An amplitude (magnitude of current) of the current "ccin" is made variable by a magnitude of the voltage of the transition setting signal tn.

The current "ccin" draws electric charges first from the gates of the transistors MN8 and MP8 of the buffer unit 57, and therefore, as shown in FIG. 6, a current having absolute value flows. Thereafter, the absolute value of the current "ccin" is gradually reduced while electric charges of the gates of the current transistors MN8 and MP8 are discharged. Further, the current "ccin" flows in the resistor R1 by a constant current value.

"vin" shows voltages of gates of the transistors MN8 and MP8 of the buffer unit 57. The voltage "vin" rises by outputting the current "ccip" of the current controlling current source unit 54.

A transition time of the rise of the voltage "vin" can be made variable by a magnitude of the current "ccip" outputted from the current controlling current source unit 54. As described above, the magnitude of the current "ccip" is made variable by the transition time setting signal tp, and therefore, the transition time of the rise of the voltage "vin" is made variable by the transition time setting signal tp.

Further, the larger the absolute value of the current "ccip", the faster the gate voltages of the transistors MN8 and MP8 of the buffer unit 57 rise, and therefore, the transition time of the rise of "vin" is shortened. Further, the smaller the absolute value of the current "ccip", the more slowly gate voltages of the transistors MN8 and MP8 of the buffer unit 57 rise, and therefore, a transition time of rise of "vin" is prolonged.

Further, the voltage "vin" falls by drawing the current "ccin" by the current controlling current source unit 54.

A transition time of the fall of the voltage "vin" can be made variable by a magnitude of the current "ccin" drawn from the current controlling current source unit 54. As described above, a magnitude of the current "ccin" is made variable by the transition time setting signal tn, and therefore, a transition time of the fall of the voltage "vin" is made variable by the transition time setting signal tn.

Further, the larger the absolute value of the current "ccin", the faster the gate voltages of the transistors MN8 and MP8 of the buffer unit 57 fall, and therefore, the transition time of the fall of "vin" is shortened. Further, the smaller the absolute value of the current "ccin", the more slowly the gate voltages of the transistors MN8 and MP8 of the buffer unit 57 fall, and therefore, the transition time of the fall of "vin" is prolonged.

Further, the voltage "vin" rises to the voltage in accordance with a voltage supplied to the source of the transistor MN6 of the current controlling current source unit 53. The source voltage of the transistor MN6 of the current controlling current source unit 53 is made variable by a voltage of the amplitude setting signal ap supplied to a gate of the amplitude controlling transistor MN7, and therefore, amplitude when the voltage "vin" rises is made variable by a voltage of the amplitude setting signal ap.

Further, the voltage "vin" falls down to the voltage in accordance with a voltage supplied to the source of the transistor MP6 of the current controlling current source unit 54. A source voltage of the transistor MP6 of the current controlling current source unit 54 is made variable by a voltage of the amplitude setting signal an supplied to the gate of the amplitude controlling transistor MP7, and therefore, amplitude when the voltage "vin" falls is made variable by the amplitude setting signal an.

"out" indicates source voltages of the transistors MN8 and MP8 of the buffer unit 57. An amplitude of the voltage "out" is reduced relative to the voltage "vin" by an amount of a threshold voltage of the transistors MN8 and MP8 of the buffer unit 57 in contrast to the voltage "vin".

Figure 7:
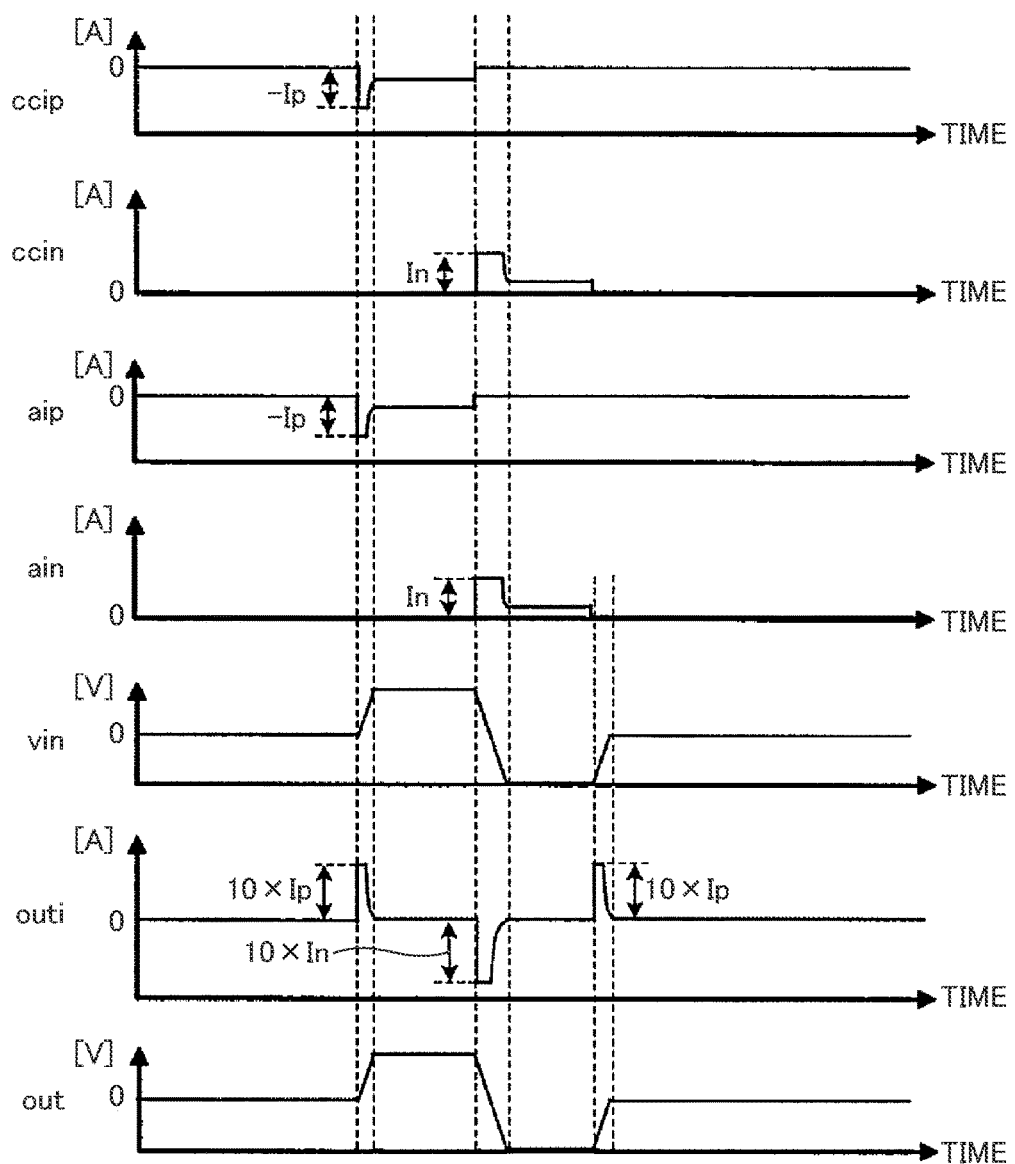
FIG. 7 is a diagram part 2 showing a timing chart of the wave transmitting circuit of FIG. 5.

FIG. 7 is part 2 of a diagram showing timing charts of the wave transmitting circuit of FIG. 5. "ccip", "ccin", "vin", and "out" shown in FIG. 7 are similar to "ccip", "ccin", "vin", and "out" shown in FIG. 6, and a detailed explanation thereof will be omitted.

"-Ip" shown in "ccip" of FIG. 7 indicates a magnitude "amplitude" of a current outputted from the current controlling current source unit 53 to gates of the transistors MN8 and MP8 of the buffer unit 57 when an electric charge is charged.

"In" shown in "ccin" indicates a magnitude (amplitude) of a current drawn from the current controlling current source unit 54 when an electric charge is discharged from the gates of the transistors MN8 and MP8 of the buffer unit 57. "aip" indicates a current flowing in the transistor MN7 of the amplitude control unit 55. The amplitude control unit 55 is connected between the power source HVDD and the current controlling current source unit 53, and therefore, the current "aip" is similar to the current "ccip" flowing in the current controlling current source unit 53. That is, the amplitude control unit 55 changes a voltage supplied to the current controlling current source unit 53 based on the amplitude setting signal ap, and supplies the current from the power source HVDD to the current controlling current source unit 53.

"ain" indicates a current flowing in the transistor MP7 of the amplitude control unit 56. The amplitude control unit 56 is connected between the power source HVSS and the current controlling current source unit 54, and therefore, the current "ain" is similar to the current "ccin" flowing in the current controlling current source unit 54. That is, the amplitude control unit 56 changes a voltage supplied to the current controlling current source unit 54 based on the amplitude setting signal an, and makes a current drawn by the current controlling current source unit 54 flow to the power source HVSS.

"outi" indicates a current outputted from the sources of the transistors MN8 and MP8 of the buffer unit 57. "10× Ip" shown by the current "outi" indicates amplitude of the output current of the buffer unit 57 when the current of the amplitude "-Ip" is outputted from the current controlling current source unit 53 to the buffer unit 57. Further, "10× In" indicated at the current "outi" indicates amplitude of the output current of the buffer unit 57 when the current controlling current source unit 53 draws a current of amplitude "In" from the buffer unit 57. In FIG. 7, an example in which the buffer unit 57 outputs a current 10 times as much as an input current to the input current is shown.

Figure 8:
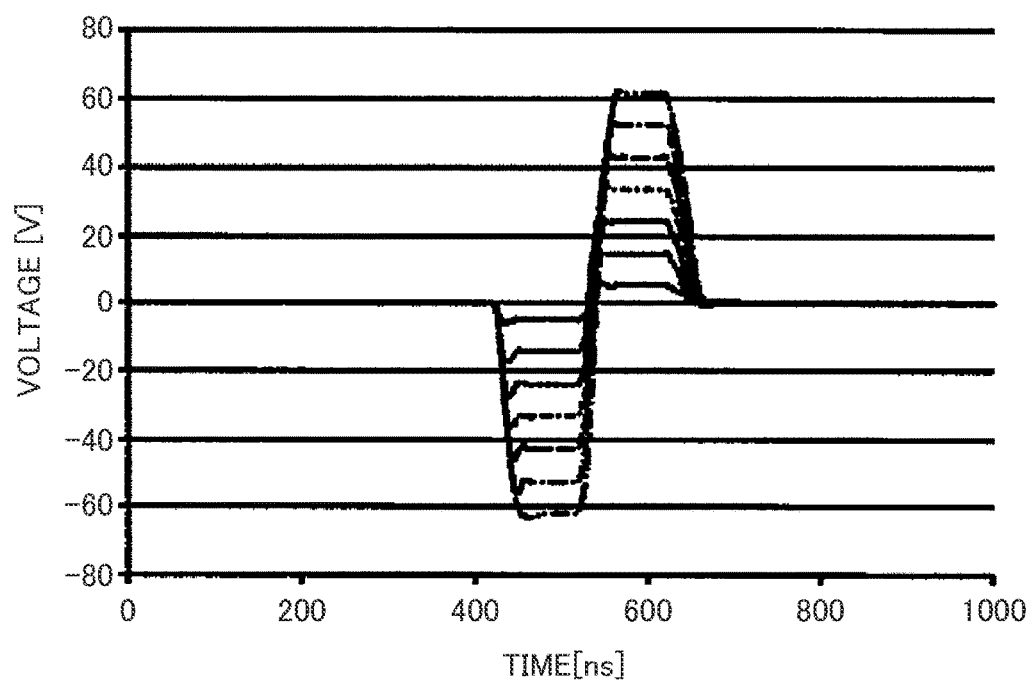
FIG. 8 is a diagram showing a simulation result of amplitude control of the wave transmitting circuit of FIG. 5.

FIG. 8 is a diagram showing a simulation result of amplitude control of the wave transmitting circuit of FIG. 5. FIG. 8 shows a simulation result of the drive signal out outputted from the buffer unit 57 of the wave transmitting circuit 33 for 7 kinds of amplitude setting signals ap and an.

The wave transmitting circuit 33 can make amplitude of the drive signal out outputted from the buffer unit 57 variable by the amplitude setting signals ap and an inputted to the variable current source unit 51. For example, as shown in FIG. 8, the wave transmitting circuit 33 can make amplitude when the drive signal out falls variable by the inputted amplitude setting signal an. Further, the wave transmitting circuit 33 can make amplitude when the drive signal out rises variable by the inputted amplitude setting signal ap.

Figure 9:
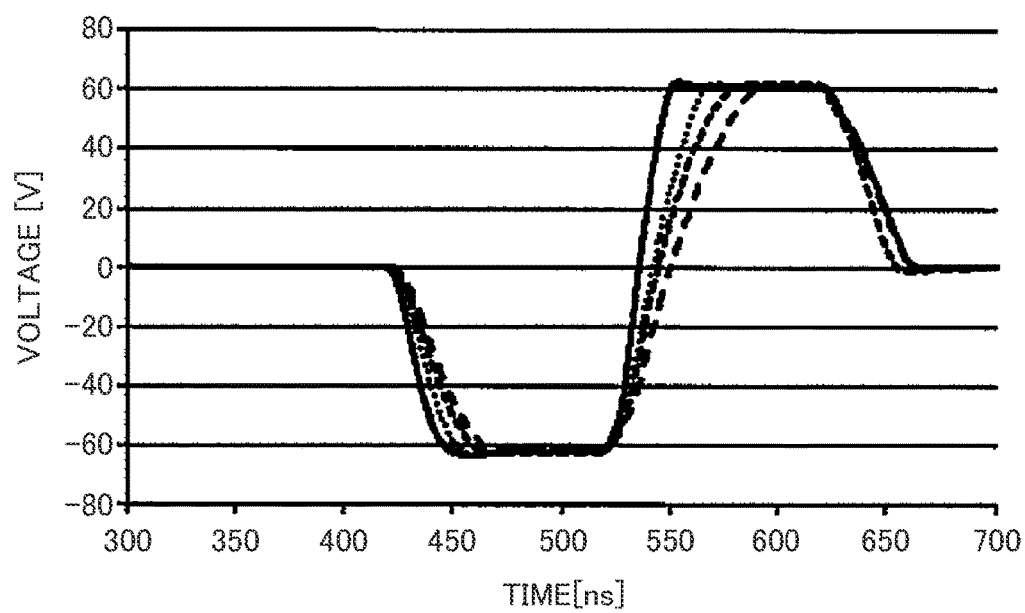
FIG. 9 is a diagram showing a simulation result of a transition time control of the wave transmitting circuit of FIG. 5.

FIG. 9 is a diagram showing a simulation result of the transition time control of the wave transmitting circuit of FIG. 5. FIG. 9 shows a simulation result of the drive signal out outputted from the buffer unit 57 of the wave transmitting circuit 33 for four kinds of transition time setting signals tp and tn.

The wave transmitting circuit 33 can make transition times of rises and falls of the drive signal out outputted from the buffer unit 57 variable by the transition setting signals tp and tn inputted to the variable current source unit 51. For example, as shown in FIG. 8, the wave transmitting circuit 33 can adjust a transition time of a fall of the drive signal out by the inputted transition time setting signal tn. Further, the wave transmitting circuit 33 can adjust a transition time of a rise of the drive signal out by the inputted transition time setting signal tp.

In this way, the wave transmitting circuit 33 includes the current controlling current source unit 53 for changing an outputted current based on the transition time setting signal tp, the current controlling current source unit 54 for changing a drawn current based on the transition time setting signal tn, the amplitude control unit 55 for changing a power source voltage supplied to the current controlling current source unit 53 based on amplitude setting signal ap, and changing amplitude of a voltage generated by a current outputted from the current controlling current source unit 53, amplitude control unit 56 for changing a power source voltage supplied to the current controlling current source unit 54 based on the amplitude setting signal an, and changing amplitude of a voltage generated by a current drawn by the current controlling current source unit 54, and the buffer unit 57 for driving a load in accordance with a current outputted from the current controlling current source unit 53 and a current drawn from the current controlling current source unit 54.

Thereby, the wave transmitting circuit 33 can be divided into the buffer unit 57 for driving the load, the current controlling current source units 53 and 54 and the amplitude control units 55 and 56 for controlling the transition time and the amplitude of the signal outputted from the buffer unit 57, a transistor for a large current for driving the load can be used at the buffer unit 57, transistors for a small current can be used in the current controlling current source units 53 and 54 and the amplitude control units 55 and 56, and a signal can be amplified by a small circuit size.

For example, suppose that the transistor for the large current for a high voltage withstanding use can make a current ten times as much as a small current flow to the transistor for the small current for high voltage withstanding use. In this case, a size of the transistor for the small current of the high voltage withstanding use becomes a size of about $\frac{1}{10}$ of the size of the transistor for large current of a high voltage withstanding use. Therefore, when, for example, 10 of the transistors for small current of the high voltage withstanding use are used, its size becomes a size similar to a size of one piece of the transistor for large current of high voltage withstanding used. In the wave transmitting circuit of FIG. 5, there are two of the transistors for large current of high voltage withstanding use, and eight of the transistors for small current of high voltage withstanding use (size smaller than one piece of transistor for large current of high voltage withstanding use), and the size is smaller than a size of an amplifying circuit in a case where four transistors for large current are used. Further, an increase in power consumption can be restrained.

[Second Embodiment]

It is preferable that when the output of the drive signal is finished, the wave transmitting circuit converges the drive signal immediately to a reference voltage (for example, voltage of power source VSS). Because when a converging speed is slow, a low frequency component is included in the drive signal, and a resolution of an ultrasonic probe is reduced. In a second embodiment, an explanation will be given of a circuit increasing a converging speed of the drive signal to the reference voltage when an output of the drive signal is finished.

Figure 10:
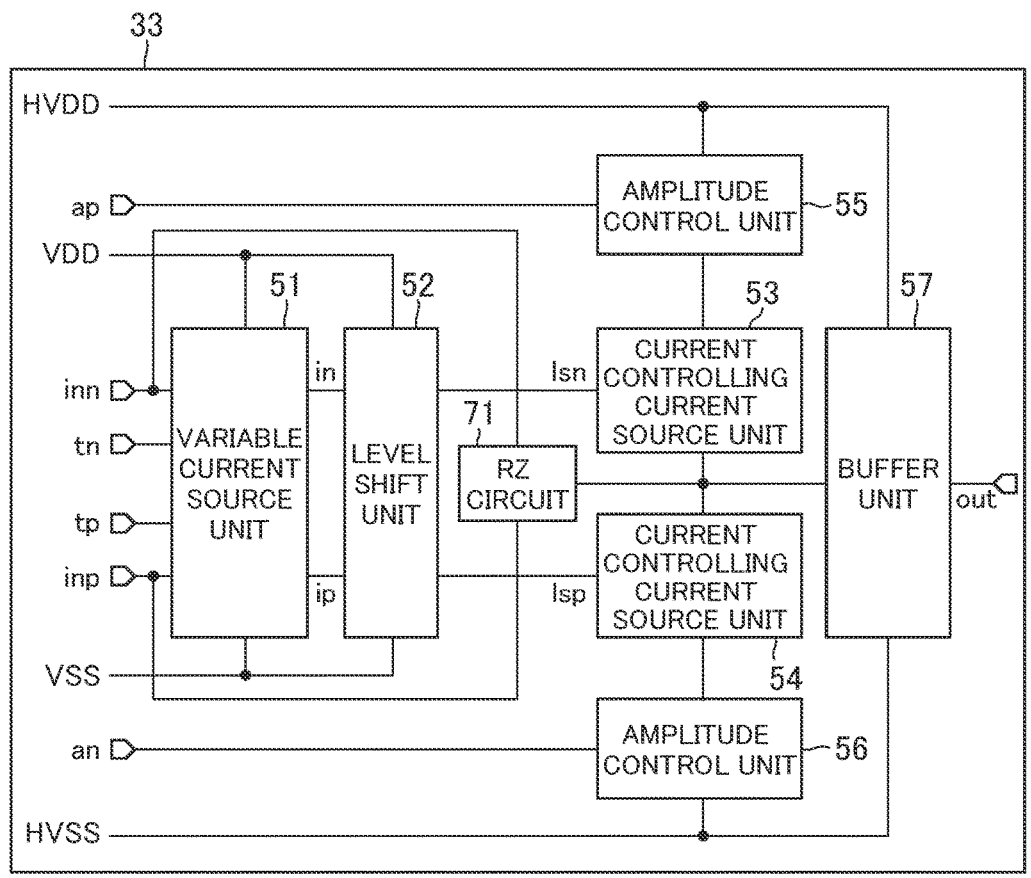
FIG. 10 is a diagram showing a block diagram of a wave transmitting circuit according to a second embodiment.

FIG. 10 is a diagram showing a block example of a wave transmitting circuit according to the second embodiment. In FIG. 10, a unit the same as that of FIG. 4 is attached with the same notation.

As shown in FIG. 10, the wave transmitting circuit 33 includes an RZ (Return to zero) circuit 71. The RZ circuit 71 is inputted with input signals inp, and inn. An output of the RZ circuit 71 is connected to an input of the buffer unit 57.

Figure 11:
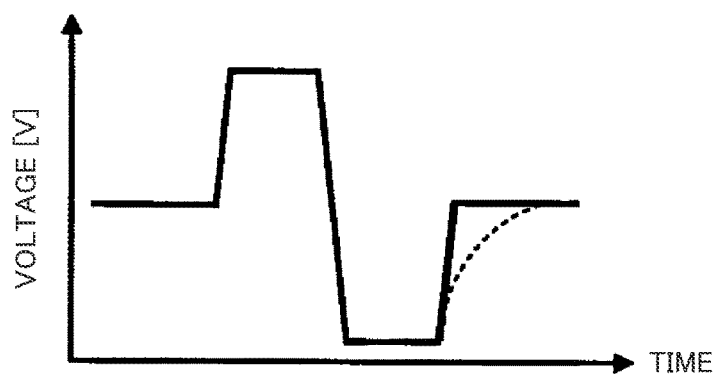
FIG. 11 is a diagram for explaining convergence of a drive signal.

FIG. 11 is a diagram for explaining a convergence of the drive signal. FIG. 11 shows a waveform of the drive signal out outputted from the buffer unit 57.

There is a case of requiring time for the drive signal out to converge to a voltage of the power source VSS (for example, ground voltage, 0V) from a fall state when an output is finished as shown in a waveform of a dotted line of FIG. 11. Hence, the RZ circuit 71 increases a converging speed of the drive signal out when an output of the drive signal out is finished as shown in a waveform of a bold line of FIG. 11.

Further, although in FIG. 11, an explanation has been given of an example in which the drive signal out rises from a fall state and converges to the reference voltage, the same goes with the case in which the drive signal falls from a rise state and converges to the reference voltage.

Figure 12:
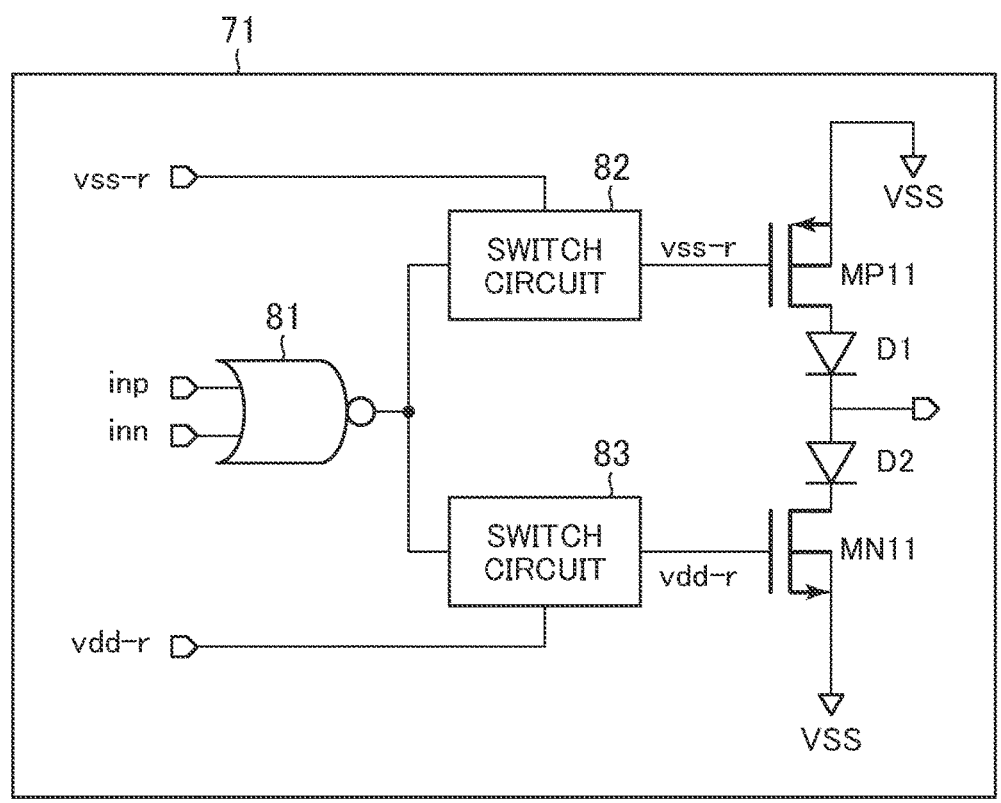
FIG. 12 is a diagram showing a circuit example of an RZ circuit of FIG. 10.

FIG. 12 is a diagram showing a circuit example of the RZ circuit of FIG. 10. As shown in FIG. 12, the RZ circuit 71 includes a NOR circuit 81, switch circuits 82 and 83, a transistor MP11 of PMOS for a high voltage withstanding use, a transistor MN11 of NMOS for high voltage withstanding use, and diodes D1 and D2.

The NOR circuit 81 is inputted with input signals inp and inn. The NOR circuit 81 outputs a signal of "L state" to the switch circuits 82 and 83 when the input signal inp or the input signal inn of "H state" is inputted. The NOR circuit 81 outputs a signal of "H state" to the switch circuits 82 and 83 when the input signal inp and the input signal inn of "L state" are inputted.

The switch circuit 82 is inputted with a signal outputted from the NOR circuit 81 and a converging signal vss-r. The converging signal vss-r is a signal for converging the fallen drive signal out to the reference voltage. For example, the converging signal vss-r is a signal for changing a signal of a waveform of a dotted line shown in FIG. 11 to a signal of a waveform of a bold line.

The converging signal vss-r is outputted, for example, from the apparatus main body 11. A magnitude of the converging signal vss-r is made variable, for example, by operating the input apparatus of the apparatus main body 11 by a user. That is, a converging time of the fallen drive signal out to the reference voltage can be adjusted by making the magnitude of the converging signal vss-r variable by a user.

The switch circuit 82 does not output the converging signal vss-r to the gate of the transistor MP11 when a signal of "L state" is inputted from the NOR circuit 81. That is, the switch circuit 82 does not output the signal of vss-r to the transistor MP11 in a case where the input signal inp or the input signal inn is outputted from the delay control circuit 32. On the other hand, the switch circuit 82 outputs the converging signal vss-r to the gate of the transistor MP11 when a signal of "H state" is inputted from the NOR circuit 81. That is, the switch circuit 82 outputs the signal vss-r to the transistor MP11 in a case where the input signal inp and the input signal inn are not outputted from the delay control circuit 32.

The switch circuit 83 is inputted with a signal outputted from the NOR circuit 81 and the converging signal vdd-r. The converging signal vdd-r is a signal for converging a risen drive signal out to a reference voltage.

The converging signal vdd-r is outputted from, for example, the apparatus main body 11. A magnitude of the converging signal vdd-r is made variable, for example, by operating the input apparatus of the apparatus main body 11 by a user. That is, the user can adjust the converging time of the risen drive signal out to a reference voltage by making the magnitude of the converging signal vdd-r.

The switch circuit 83 does not output the converging signal vdd-r to the gate of the transistor MN11 when a signal of "L state" is inputted from the NOR circuit 81. That is, the switch circuit 83 does not output the signal vdd-r to the transistor MN11 in a case where the input signal inp or the input signal is outputted from the delay control circuits 132. On the other hand, the switch circuit 83 outputs the converging signal vdd-r to the gate of the transistor MN11 when a signal of "H state" is inputted from the NOR circuit 81. That is, the switch circuit 83 outputs the signal vdd-r to the transistor MN11 in a case where the input signal inp and the input signal inn are not outputted from the delay control circuit 32.

The gate of the transistor MP11 is connected to an output of the switch circuit 82. The source of the transistor MP11 is connected to the power source VSS. The drain of the transistor MP11 is connected to an anode of a diode D1. The transistor MP11 is made ON and connects an input of the buffer unit 57 to the power source VSS when the converging signal vss-r is outputted from the switch circuit 82. At that time, a current in accordance with a magnitude of the voltage of the converging signal vss-r inputted to the gate flows in the transistor MP11.

The gate of the transistor MN11 is connected to an output of the switch circuit 83. The source of the transistor MN11 is connected to the power source VSS. The drain of the transistor MN11 is connected to a cathode of a diode D2. The transistor MN11 is made ON and connects an input of the buffer unit 57 to the power source VSS when the converging signal vdd-r is outputted from the switch circuit 83. At that time, a current in accordance with a magnitude of the voltage of the converging signal vdd-r inputted to the gate flows to the transistor MN11.

The anode of the diode D1 is connected to the drain of the transistor MP11. A cathode of the diode D1 is connected to an anode of the diode D2 and connected to a connecting point of the current controlling current source unit 53 and 54 and the buffer unit 57. The diode D1 prevents a current from flowing from the buffer unit 57 to the transistor MP11.

A cathode of the diode D2 is connected to the drain of the transistor MN11. An anode of the diode D2 is connected to a cathode of the diode D1, and connected to a connecting point of the current controlling current source units 53 and 54 and the buffer unit 57. The diode D2 prevents a current from flowing from the power source VSS to the transistor MN11.

An explanation will be given of an operation of the RZ circuit 71 by using timing charts.

Figure 13:
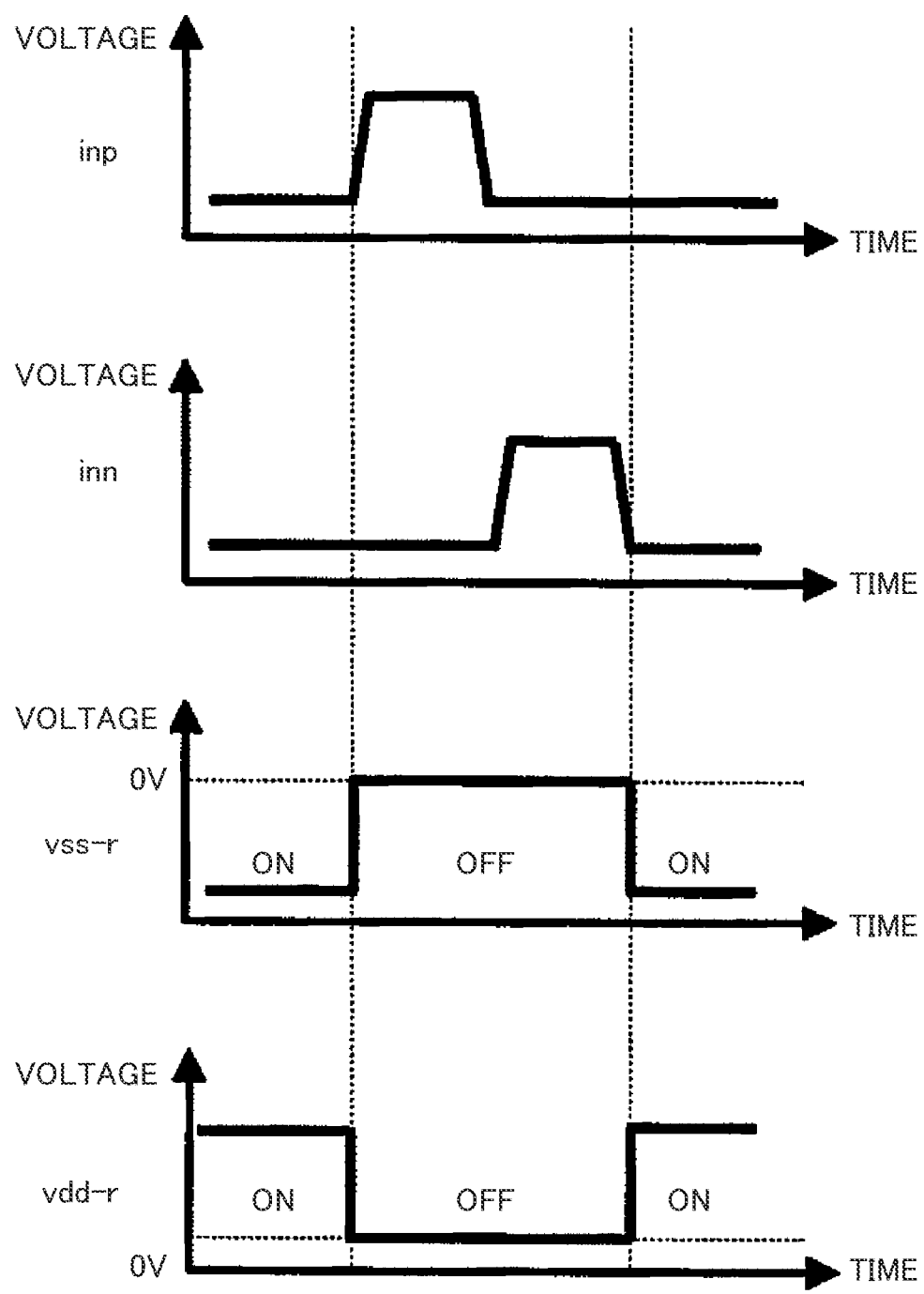
FIG. 13 is a diagram showing a timing chart of an RZ circuit of FIG. 12.

FIG. 13 is a diagram showing timing charts of the RZ circuit of FIG. 11. "inp" shown in FIG. 13 indicates a voltage of the input signal inp outputted from the delay control circuit 32.

"inn" indicates a voltage of the input signal inp outputted from the delay control circuit 32.

"vss-r" indicates a voltage outputted from the switch circuit 82 to the gate of the transistor MP11.

"vdd-r" indicates a voltage outputted from the switch circuit 83 to the gate of the transistor MN11.

The switch circuits 82 and 83 output the converging signal vss-r and the converging signal vdd-r to the transistors MP11 and MN11 when the input signal inp and the input signal inn are brought into "L state" as shown in FIG. 13. That is, the switch circuits 82 and 83 output the converging signal vss-r and the converging signal vdd-r to the transistors MP11 and MN11 when the current controlling current source unit 53 finishes an output of the current, and an output of the drive signal out is finished, or when the current controlling current source unit 54 finishes drawing a current and an output of the drive signal out is finished. Thereby, when the output of the drive signal out is finished, the transistors MP11 and MN11 are made ON, and an input of the buffer unit 57 is connected to the power source Vss. Further, currents in accordance with the converging signal vss-r and the converging signal vdd-r flow to one of the transistors MP11 and MN11.

For example, if a signal of the input of the buffer unit 57 falls when an output of the drive signal out is finished, a current in accordance with the converging signal vss-r flows to the transistor MP11. If a signal of an input of the buffer unit 57 rises when the output of the drive signal out is finished, a current in accordance with the converging signal vdd-r flows to the transistor MN11.

In this way, the wave transmitting circuit 33 includes the RZ circuit 71 for converging the voltage of the input of the buffer unit 57 to the power source VSS when the current controlling current source unit 53 finishes outputting the current and when the current controlling current source unit 54 finishes drawing the current. Thereby, the wave transmitting circuit 33 can increase a converging speed of the drive signal to the reference voltage.

Further, the wave transmitting circuit 33 can restrain a low frequency component included in the drive signal out, and can restrain a reduction in a resolution of the ultrasonic probe.

Further, the converging signals vss-r and vdd-r are inputted to the gates of the transistor MP11 and MN11 of the RZ circuit 71, and therefore, a user can adjust the converging speed of the drive signal out by adjusting magnitudes of the converging signals vss-r and vdd-r.

The present invention is not limited to the embodiments described above but includes various modified examples. For example, the embodiments described above explain in detail the whole of a system for explaining the present invention to be easy to understand and are not necessarily limited to an example including all of the configurations explained. Further, a portion of a configuration of a certain embodiment can be replaced by a configuration of other embodiment, further, a configuration of other embodiment can be added to a configuration of a certain embodiment. Further, another configuration can be added, deleted, or replaced concerning a portion of a configuration of each embodiment. Further, a portion or all of each configuration, function, processing unit, processing means or the like described above may be realized by hardware by, for example, designing the amplifier portion or the total by an integrated circuit. Further, a circuit of the wave transmitting circuit 33 described above can be applied also to an apparatus for amplifying a signal.

LIST OF REFERENCE SIGNS

11: apparatus main body,
12: ultrasonic probe,
12a: 2D array oscillator,
12b: 2D array IC,
21: sub array,
22, 23 surrounding circuits,
31: element circuit,
32: delay control circuit,
33: wave transmitting circuit,
34: receiving circuit,
41: oscillator,
51: variable current source unit,
52: level shift unit,
53, 54: current controlling current source units,
55, 56: amplitude control units,
57: buffer unit,
61, 62: inverters,
71: RZ circuit,
81: NOR circuit,
82, 83: switch circuits

The invention claimed is:

1. An amplifier circuit comprising:
a first current source unit for changing an outputting current based on a first setting signal;
a second current source unit for changing a drawing current based on a second setting signal;
a first amplitude control unit for changing a power source voltage supplied to the first current source unit and changing amplitude of a voltage generated by the current outputted from the first current source unit based on a third setting signal;
a second amplitude control unit for changing a power source voltage supplied to the second current source unit and changing amplitude of a voltage generated by the current drawn by the second current source unit based on a fourth setting signal;
a buffer unit for driving a load in accordance with the current outputted from the first current source unit and the current drawn from the second current source unit;
a third current source unit inputted with the first setting signal, outputting a first setting current in accordance with a magnitude of the first setting signal, inputted with the second setting signal, and outputting a second setting current in accordance with a magnitude of the second setting signal,
wherein the first current source unit changes the current outputted based on the magnitude of the first setting current outputted from the third current source unit,
wherein the second current source unit changes the current drawn based on the magnitude of the second setting current outputted from the third current source unit,
wherein the first current source unit and the second current source unit are connected in series,
wherein the first amplitude control unit is connected to a first polarity of a power source and the first current source unit, changes the power source voltage supplied to the first current source unit, and supplies a current outputted by the first current source unit from the power source,
wherein the second amplitude control unit is connected between a second polarity of the power source and the second current source unit, changes the power source voltage supplied to the second current source unit, and makes the current drawn by the second current source unit flow to the power source, and
wherein the buffer unit is connected between the first polarity and the second polarity of the power source, and an input is connected between the first current source unit and the second current source unit connected in series.

2. The amplifier circuit according to claim 1,
wherein the third current source unit is supplied with a voltage from a low voltage current source lower than the power source.

3. An amplifier circuit comprising:
a first current source unit for changing an outputting current based on a first setting signal;

a second current source unit for changing a drawing current based on a second setting signal;
a first amplitude control unit for changing a power source voltage supplied to the first current source unit and changing amplitude of a voltage generated by the current outputted from the first current source unit based on a third setting signal;
a second amplitude control unit for changing a power source voltage supplied to the second current source unit and changing amplitude of a voltage generated by the current drawn by the second current source unit based on a fourth setting signal;
a buffer unit for driving a load in accordance with the current outputted from the first current source unit and the current drawn from the second current source unit; and
a converging circuit for converging a voltage of an input of the buffer unit to a reference voltage when the first current source unit finishes outputting the current and when the second current source unit finishes drawing the current.

4. An amplifier circuit comprising:
a first current source unit for changing an outputting current based on a first setting signal;
a second current source unit for changing a drawing current based on a second setting signal;
a first amplitude control unit for changing a power source voltage supplied to the first current source unit and changing amplitude of a voltage generated by the current outputted from the first current source unit based on a third setting signal;
a second amplitude control unit for changing a power source voltage supplied to the second current source unit and changing amplitude of a voltage generated by the current drawn by the second current source unit based on a fourth setting signal; and
a buffer unit for driving a load in accordance with the current outputted from the first current source unit and the current drawn from the second current source unit,
wherein the first current source unit includes a first transistor circuit for outputting the current in accordance with a magnitude of the first setting signal,
wherein the second current source unit includes a second transistor circuit for drawing the current in accordance with a magnitude of the second setting signal,
wherein the first amplitude control unit includes a first transistor a drain of which is connected to a first polarity of a power source, a source of which is connected to the first transistor circuit, and a gate of which is inputted with the third setting signal,
wherein the second amplitude control unit includes a second transistor a drain of which is connected to a second polarity of the power source, a source of which is connected to the second transistor, and a gate of which is inputted with the fourth setting signal,
wherein the buffer unit includes a third transistor in which the buffer unit includes a third transistor outputting a current from the first polarity of the power source to the load in accordance with the current outputted from the first transistor circuit, and a fourth transistor drawing a current from the load to the second polarity of the power source in accordance with the current drawn from the second transistor circuit, and
wherein sizes of the transistor configuring the first transistor circuit, the transistor configuring the second transistor circuit, the first transistor, and the second transistor are smaller than sizes of the third transistor and the fourth transistor.

5. An amplifier circuit comprising:
a first current source unit for changing an outputting current based on a first setting signal;
a second current source unit for changing a drawing current based on a second setting signal;
a first amplitude control unit for changing a power source voltage supplied to the first current source unit and changing amplitude of a voltage generated by the current outputted from the first current source unit based on a third setting signal;
a second amplitude control unit for changing a power source voltage supplied to the second current source unit and changing amplitude of a voltage generated by the current drawn by the second current source unit based on a fourth setting signal;
a buffer unit for driving a load in accordance with the current outputted from the first current source unit and the current drawn from the second current source unit,
wherein the first current source unit includes a first transistor circuit for outputting the current in accordance with a magnitude of the first setting signal,
wherein the second current source unit includes a second transistor circuit for drawing the current in accordance with a magnitude of the second setting signal,
wherein the first amplitude control unit includes a first transistor a drain of which is connected to a first polarity of a power source, a source of which is connected to the first transistor circuit, and a gate of which is inputted with the third setting signal,
wherein the second amplitude control unit includes a second transistor a drain of which is connected to a second polarity of the power source, a source of which is connected to the second transistor, and a gate of which is inputted with the fourth setting signal, and
wherein the buffer unit includes a third transistor in which the buffer unit includes a third transistor outputting a current from the first polarity of the power source to the load in accordance with the current outputted from the first transistor circuit, and a fourth transistor drawing a current from the load to the second polarity of the power source in accordance with the current drawn from the second transistor circuit;
a fifth transistor a gate of which is inputted with the first setting signal, and which outputs a first setting current in accordance with a magnitude of a voltage of the first setting signal to the first transistor circuit;
a sixth transistor a gate of which is inputted with the second setting signal and which outputs a second setting current in accordance with a magnitude of a voltage of the second setting signal to the second transistor circuit;
a seventh transistor for shifting a level of the first setting current outputted from the fifth transistor; and
an eighth transistor for shifting a level of the second setting current outputted from the sixth transistor.

6. The amplifier circuit according to claim 5,
wherein sizes of the fifth transistor, the sixth transistor, the seventh transistor, and the eighth transistor are smaller than sizes of the third transistor and the fourth transistor.

7. An ultrasonic probe comprising:
a first current source unit for changing an outputting current based on a first setting signal;

a second current source unit for changing a drawing current based on a second setting signal;

a first amplitude control unit for changing a power source voltage supplied to the current source unit, and changing amplitude of a voltage generated by a current outputted from the first current source unit based on a third setting signal;

a second amplitude control unit for changing a power source voltage supplied to the second current source unit, and changing amplitude of a voltage generated by a current drawn by the second current source unit based on a fourth setting signal;

a buffer unit for driving an oscillator emitting an ultrasonic wave in accordance with the current outputted form the first current source unit and the current drawn from the second current source unit; and a converging circuit for converging a voltage of an input of the buffer unit to a reference voltage when the first current source unit finishes outputting the current and when the second current source unit finishes drawing the current.

* * * * *